United States Patent [19]

Beregi et al.

[11] 3,972,994
[45] Aug. 3, 1976

[54] DISUBSTITUTED AZABICYCLOALKANES
[75] Inventors: Laszlo Beregi, Boulogne, Seine;
Pierre Hugon, Rueil-Malmaison;
Xavier Pascaud, Paris; Jean-Claude
Poignant, Bures, Yvette, all of
France
[73] Assignee: Science Union et Cie,
Neuilly-sur-Seine, France
[22] Filed: Nov. 20, 1974
[21] Appl. No.: 525,623

[30] Foreign Application Priority Data
Dec. 14, 1973 United Kingdom............... 58034/73

[52] U.S. Cl............................ 424/274; 260/326.1;
260/325 PH; 260/326.27; 260/326.5 B;
260/326.85; 260/326.9
[51] Int. Cl.²................. C07D 209/44; A61K 31/40
[58] Field of Search.................. 260/326.1; 424/274

Primary Examiner—Lewis Gotts
Assistant Examiner—S. P. Williams
Attorney, Agent, or Firm—Gordon W. Hueschen

[57] ABSTRACT

Disubstituted azabicycloalkanes of the formula

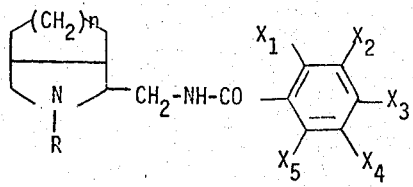

wherein:
  $n$ is 0, 1 or 2
  R is saturated or unsaturated straight or branched
    ($C_1$–$C_5$) aliphatic hydrocarbon, and
  $X_1$, $X_2$, $X_3$, $X_4$, $X_5$, which are the same or different,
    are hydrogen, halogen, hydroxy, lower alkyl,
    lower alkoxy, trifluoromethyl, nitro, amino or
    sulfamoyl.

These compounds are used as medicine especially in
the treatment of gastroduodenal ulcers, gastric
hypersecretion, nauseous syndromes of central origin
and hypertension.

15 Claims, No Drawings

DISUBSTITUTED AZABICYCLOALKANES

The present invention provides disubstituted azabicycloalkanes of the general formula I:

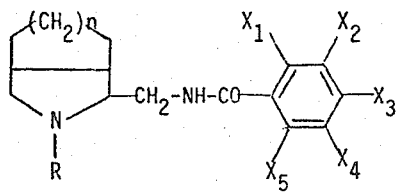

wherein:
  n is selected from 0, 1 and 2;
  R is selected from the group consisting of saturated and unsaturated aliphatic hydrocabon radical having from 1 to 5 carbon atoms inclusive in straight and branched chain and,
  $X_1$, $X_2$, $X_3$, $X_4$, and $X_5$, which are the same or different, are each selected from the group consisting of a hydrogen atom, halogen atoms, a hydroxy radical, alkyl and alkoxy radicals, each having from 1 to 5 carbon atoms inclusive, trifluoromethyl, nitro, amino and sulfamoyl radicals.

As aliphatic hydrocarbon radicals, cited for the meaning of R, there may be mentioned, for example, methyl, ethyl, propyl, butyl, allyl, methylpropenyl and butenyl radicals.

In the meaning of $X_1$, $X_2$, $X_3$, $X_4$ and $X_5$, there may be mentioned, for example, as halogen atoms: fluorine, chlorine and bromine atoms, as lower alkyl radicals: methyl, ethyl and propyl radicals, and as lower alkoxy radicals: methoxy, ethoxy and propoxy radicals.

Though all the compounds of the present invention possess valuable pharmacological properties, the compounds of the general formula I, wherein n is selected from 1 and 2, R is selected from ethyl and allyl and the phenyl nucleus of the benzamido moiety is mono-, di- or trisubstituted, are particularly interesting and, for these compounds, the preferred meanings for the X substituents are halogen, alkoxy, amino and sulfamoyl.

The present invention also provides acid addition salts, especially physiologically tolerable acid addition salts, of compounds of the general formula I with the mineral and organic acids. As acid which may be used for the formation of these salts, there may be mentioned, for example, in the mineral series: hydrochloric, hydrobromic, sulfuric and phosphoric acids, and in the organic series: acetic, propionic, maleic, fumaric, tartaric, citric, oxalic, benzoic and methanesulfonic acids.

The compounds of the general formula I are new and were prepared according to the following processes which are included in the present invention.

The present invention provides a process for preparing a compound of the general formula I which comprises:

treating an azabicycloalkanone of the general formula II:

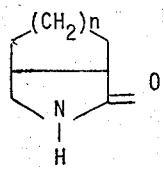

with an halide of the general formula III

Hal — R    III wherein Hal represents a halogen atom, in the presence of sodium hydride;

treating the so-obtained compound of the general formula IV

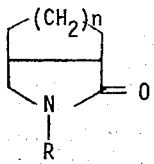

respectively with dimethyl sulfate, sodium methylate and nitromethane.

reducing the so-formed nitro compound of the general formula V

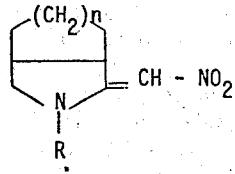

in the presence of Raney Nickel or lithium aluminium hydride then condensing the resulting -aminomethyl-azabicycloalkane of the general formula VI

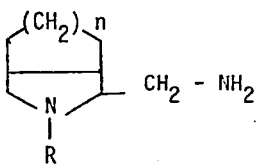

VI with the substituted benzoyl chloride of the general formula VII

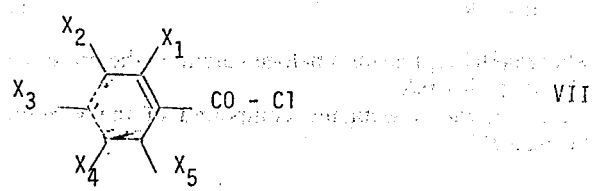

VII $n$, R, $X_1$, $X_2$, $X_3$, $X_4$, and $X_5$ having in these formulae the same meanings as in formula I.

The reaction of compounds II and III in the presence of sodium hydride is suitably caried out in an anhydrous hydrocarbon such, for example, as xylene.

The reduction of the compound V is easily performed under a hydrogen pressure of about 5 kg/m2, in the presence of Raney nickel or lithium aluminium hydride in an anhydrous alcohol such, for example, as methanol.

The condensation of compounds VI et VII is carried out in an anydrous solvent such, for example, as tetrahydrofuran in the presence of an acceptor for the hydrochloric acid formed during the reaction, such, for example, as triethylamine.

The compounds of the general formula IV, V and VI are new and are included in the present invention together with the above mentioned process for preparing them. These compounds IV, V and VI are useful intermediates for the synthesis of compounds of the formula I.

The present invention also provides a process for preparing a compound of the general formula I wherein at least one of the substituents $X_1$, $X_2$, $X_3$, $X_4$ and $X_5$ is an amino group, which comprises condensing the here above defined -aminomethyl-azabicycloalkane of the general formuala VI with an acetylamino benzoic acid of the general formula VIII

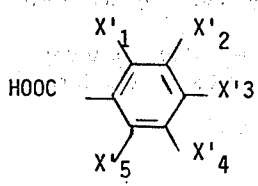

wherein at least one of the substituents $X'_1$, $X'_2$, $X'_3$, $X'_4$ and $X'_5$ is an acetylamino radical and the others have the same meanings as $X_1$, $X_2$, $X_3$, $X_4$, and $X_5$ excepted the value amino, then deacetylating the so-obtained compound of the general formula IX

IX wherein $n$, R, $X'_1$, $X'_2$, $X'_3$, $X'_4$ and $X'_5$ are as defined above.

Such adeacetylation is easily carried out by heating the compound IX with an hydro alcoholic solution of sodium hydroxide.

The compounds of the general formula I and physiologically tolerable acid addition salts thereof, possess valuable pharmacological and therapeutic properties, especially antiemetic, gastric evacuation stimulating, gastric antisecretory, central nervous system depressing and hypotensive properties.

Their toxicity is low and their $LD_{50}$ determined in fasting mice varies from 60 to 750 mg/kg by intraperitoneal route.

The antiemetic activity was evidenced in the dog by the determination of the dose which inhibits the vomiting provoked by a subcutaneous injection of 100 µg/kg of apomorphine. It was demonstrated that the antiemetic activity of the compounds of the present invention, observed as well by oral route as by injectable route, is higher than the one of Sulpiride.

It was also observed that the compounds of the present invention possess a stimulating activity on the gastric evacuation; this property was studied by D. A. Brodie and S. K. Kundratz'technic (Fed. Proc. 25, 714,1965) by measuring the evacuation rate of pellets of amberlite calibrated to 1 mm, which was introduced by intubation in fasting rats, the day before the test. By subcutaneous route, the products of the invention show an average effective dose ($ED_{50}$) lower than those of the best product of reference.

The inhibiting activity on the gastric secretions was evidenced in rats, for the compounds of the present invention, according to the method of H. G. Shay et al. (gastroent. 5, 43,1945); there was observed a decrease of 40 to 60 % of the output of acidity, 4 hours after the ligation of pylorus, at the doses ranged from 20 to 30 mg/kg by intraperitoneal and intraduodenal routes.

The neurological examination of mice and rats treated with the compounds of the present invention shows a decrease of the motility together with a notable decrease of conditioned reflexes in Skinner box.

Furthermore, an hypotensive activity in the anesthetized dog was found for the compounds of the present invention owed to their adrenolytic property.

The low toxicity and the above described pharmacological properties enable the use of the compounds of the present invention in therapy, especially in the treatment of gastroduodenal ulcers, gastric hypersecretion, nauseous syndromes of central origin and hypertension.

The present invention also provides a pharmaceutical preparation which contains a compound of the general formula I or a physiologically tolerable salt thereof in admixture or conjunction with a pharmaceutically suitable carrier such, for example, as distilled water, talc, starch, glucose or cocoa butter.

The so-obtained pharmaceutical preparations are advantageously in unit dosage form and may contain from 10 to 200 mg, preferably from 20 to 100 mg, of the active ingredient.

These pharmaceutical preparations may be in form of tablets, dragees, capsules, suppositories or injectable or drinkable solutions and may be administered by oral, rectal or parenteral route at a dose of from 10 to 200 mg, preferably from 20 to 100 mg in active ingredient, one to five times a day.

The following examples illustrate the invention, the parts being by weigh and the melting points being determined on a Kofler hot plate.

EXAMPLE 1

N-ethyl-2-(2-methoxy-5-sulfamoyl benzamido methyl)-3-azabicyclo (3,3,0) octane

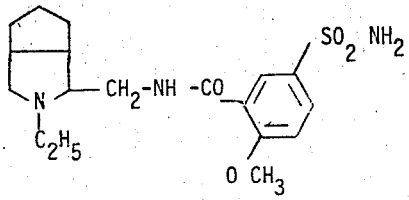

57.6 parts of sodium hydride at 50 % (1.2 mole) in paraffine were introduced in 1500 parts of anhydrous xylene. To this suspension there was added portionwise in the course of 1 hour at room temperature, a solution of 150 parts (1.2 mole) of 3-azabicyclo (3,3,0)-2-octanone in 600 parts of anhydrous xylene. The mixture was refluxed for 45 minutes. After cooling, 187 parts (1.2 mole) of ethyl iodide were added in 30 minutes, then the reaction mixture was heated for 1 hour at 110° C. After cooling, 400 parts of water were added. The organic layer separated and dried over anhydrous magnesium sulfate was concentrated in vacuo. Upon distillation, there were obtained 95.5 parts of N-ethyl-3-azabicyclo (3,3,0)-2-octanone B.P./0.2 mmHg = 76°–79° C $n_D^{25} = 1.4872$.

After extraction of the aqueous layer with 500 parts of chloroform, followed by drying concentration, the distillation gave another 46 parts of N-ethyl-3-azabicyclo (3,3,0)-2-octanone, having the same B.P. and $n_D^{25}$ than the product obtained from the organic layer.

74.7 parts (0.59 mole) of dimethyl sulfate were added in 20 minutes to 91 parts of N-ethyl-3-azabicyclo (3,3,0)-2-octanone. The reaction mixture was heated to 60°–65° C for 90 minutes. After cooling and addition of chilled water, the reaction mixture was treated with 182 parts of a 3.25 N solution of $CH_3O$ Na in methanol. After stirring at room temperature for 30 minutes, there were added 54.3 parts (0.89 mole) of nitromethane. After stirring 1 hour at room temperature, the mixture was concentrated in vacuo. The residue was treated by 200 parts of water and the so-formed precipitate dried on standing in the laboratory.

There were obtained 62.5 parts of N-ethyl-2-nitromethylene-3-azabicyclo (3,3,0) octane which after crystallization (benzene/cyclohexane) melts at 86° C.

54 parts of N-ethyl-2-nitromethylene-3-azabicyclo (3,3,0) octane, in solution in 500 parts of anhydrous methanol were reduced in presence of 20 parts of Raney Nickel at 5 kg/m2 pressure. After filtration and washing of the catalyst by methanol, the filtrate was evaporated under vacuo then distilled. There were obtained 30 parts of N-ethyl-2-aminomethyl-3-azabicyclo (3,3,0) octane, B.P./0.25–0.30 mm Hg : 88°–90° C. This reduction can be easily carried out with lithium aluminium hydride too.

To a solution of 10.77 parts of N-ethyl-2-aminomethyl-3-azabicyclo (3,3,0) octane and 6.46 parts of triethylamine in 100 parts of anhydrous tetrahydrofuran, were added portionwise a solution of 17 parts of 2-methoxy-5-sulfamoyl benzoyl chloride in 250 parts of tetrahydrofuran. After being heated to 45° C for 1 hour, the triethylamine hydrochloride was filtered off, the filtrate was diluted with 50 parts of ether.

After 24 hours, the precipitate was filtered and treated with 130 parts of boiling ethanol. After drying, there were obtained 13.5 parts of N-ethyl-2-(2-methoxy-5 sulfamoyl benzamido methyl)-3-azabicyclo (3,3,0) octane, M.P. 232° C.

2-methoxy-5-sulfamoyl benzoyl chloride here above used as starting material, was prepared as follows:

To a suspension of 125 parts (0.82 mole) of o . anisic acid in 450 parts of anhydrous chloroform, there were added in the course of 45 minutes at 0° C, 233 parts of chlorosulfonic acid. After being maintained the reaction mixture at room temperature for 90 minutes, the temperature was progressively increased and finally reflux was maintained for 90 minutes. The chloroform was separated and the residue was treated with 800 parts of water/ice while stirring. After filtration, the precipitate was washed with water and dried. There were obtained 34 parts of 2-methoxy-5-chlorosulfonyl benzoic acid, M.P. 145° C.

The so-obtained crude product was treated with 135 parts of concentrated ammonia and 135 parts of water. The reaction mixture was left to stand for 4 hours at room temperature, then 320 parts of water were added while cooling with ice. After acidification with 170 parts of concentrated HCl, the precipitated acid was filtered off, washed with water and finally dried. There were obtained 26.8 parts of 2-methoxy-5-sulfamoyl benzoic acid, M.P. 224°–225° C.

To a suspension of the so-obtained 2-methoxy-5-sulfamoyl benzoic acid in 600 parts of anhydrous tetrahydrofuran, there were added rapidly 27.5 parts of thionyl chloride. The mixture was refluxed for 2 hours. The solution was then evaporated under vacuo. The residue was treated with 500 parts of anhydrous benzene. After elimination of benzene in vacuo, there were obtained 29 parts of 2-methoxy-5-sulfamoyl benzoyl chloride, M.P. 148°–150° C, which after one recrystallization from benzene melts at 156° C.

EXAMPLES 2 TO 19

The following compounds were prepared according to the process described in example 1.

2. N-Propyl-2-(2-methoxy-5-sulfamoyl benzamido methyl)-3-azabicyclo (3,3,0) octane. Starting from 2-methoxy-5-sulfamoyl benzoyl chloride and N-propyl-2-aminomethyl-3-azabicyclo (3,3,0) octane. The latter was prepared starting from N-propyl-2-nitromethylene-3-azabicyclo (3,3,0) octane, itself prepared starting from N-propyl-3-azabicyclo (3,3,0) -2-octanone, obtained from 3-azabicyclo (3,3,0)-2-octanone.

3. N-allyl-2-(2-methoxy-5-sulfamoyl benzamido methyl)-3-azabicyclo (3,3,0) octane M.P. 163°–164° C (isopropanol), starting from 2-methoxy-5-sulfamoyl benzoyl chloride and N-allyl-2-aminomethyl-3-azabicyclo (3,3,0) octane, B.P. 5mm Hg : 112° C. The latter was prepared starting from N-allyl-2-nitromethylene-3-azabicyclo (3,3,0) octane M.P. 99°–100° C (benzene), itself prepared starting from N-allyl-3-azabicyclo (3,3,0)-2- octanone B.P. 0,4 mm Hg : 86°–88°C, obtained from 3-azabicyclo (3,3,0)-2-octanone.

4. N-ethyl-2-(2-methoxy-5-sulfamoyl benzamido methyl)-3-azabicyclo (3,3,0) heptane, starting from 2-methoxy-5-sulfamoyl benzoyl chloride and N-ethyl-2-aminomethyl-3-azabicyclo (3,2,0) heptane. The latter was prepared starting from N-ethyl-2-nitromethylene-3-azabicyclo (3,2,0) heptane, itself prepared starting from N-ethyl-3-azabicyclo (3,2,0)-2-heptanone obtained from 3-azabicyclo (3,2,0) -2- heptanone.

5. N-allyl-2- (2-methoxy-5-sulfamoyl benzamido methyl)-3-azabicyclo (3,2,0) heptane, starting from 2-methoxy-5-sulfamoyl benzoyl chloride and N-allyl-2-aminomethyl-3-azabicyclo (3,2,0) heptane. The latter was prepared starting from N-allyl-2-nitromethylene-3-azabicyclo (3,2,0) heptane, itself prepared starting from N-allyl-3-azabicyclo (3,2,0)-2-heptanone obtained from 3-azabicyclo (3,2,0)-2-heptanone.

6. N-ethyl-7-(2-methoxy-5-sulfamoyl benzamido methyl)-8-azabicyclo (4,3,0)nonano M.P. 241°–242° C with decomposition (dimethylformamide/water) starting from 2-methoxy-5-sulfamoyl benzoyl chloride and N-ethyl-7-aminomethyl-8-aza bicyclo (4,3,0) nonane B.P. /0,3 mm Hg: 76°–78° C. The latter was prepared starting from N-ethyl-2nitromethylene-8-azabicyclo (4,3,0) nonane M.P. 101°–102° C (cyclohexane), itself prepared starting from N-ethyl-8-azabicyclo (4,3,0)-7-nonanone B.P. /0,5 mm Hg : 99°–102°C, obtained from 8-azabicyclo (4,3,0)-7-nonanone.

7. N-allyl-7-(2-methoxy-5-sulfamoyl benzamido methyl)-8-azabicyclo (4,3,0) nonane, starting from 2-methoxy-5-sulfamoyl benzoyl chloride and N-allyl-7-aminomethyl-8-azabicyclo (4,3,0) nonane. The latter was prepared starting from N-allyl-7-nitromethylene-8-azabicyclo (4,3,0) nonane, itself prepared starting from N-allyl-8-azabicyclo (4,3,0)-7-nonanone, obtained from 8-azabicyclo (4,3,0) -7-nonanone.

8. N-(2-methyl-2-propenyl)-2-(2-methoxy-5-sulfamoyl benzamido methyl)-3-azabicyclo (3,3,0) otane, M.P. 183°–185°C (ethanol), starting from 2-methoxy-5-sulfamoyl benzoyl chloride and N-(2-methyl-2 propenyl)-2-aminomethyl-3-azabicyclo (3,3,0) octane, B.P./0.1mm Hg: 75°–77°C. This latter was prepared starting from N-(2-methyl-2-propenyl)-2-nitromethylene-3-azabicyclo(3,3,0) octane, M.P. 128°–129° C (isopropanol) itself prepared starting from N- (2-methyl-2-propenyl)-3-azabicyclo (3,3,0)-2-octanone, B.P. 0,3 mm Hg : 100°–102°C, obtained from 3-azabicyclo(3,3,0) -2- octanone.

9. N-ethyl-2-(2-methoxybenzamido methyl)-3-azabicyclo (3,3,0) octane, M.P. of its hydrochloride : 137°–138° C (ethyl acetate/isopropanol), starting from 2-methoxy benzoyl chloride and N-ethyl-2-aminomethyl-3-azabicyclo (3,3,0) octane.

10. N-ethyl-2-(3-trifluoromethyl benzamidomethyl)-3-azabicyclo (3,3,0) octane, M.P. 101° C (cyclohexane) starting from 3-trifluoromethylbenzoyl chloride and N-ethyl-2-aminomethyl-3-azabicyclo (3,3,0) octane.

11. N-ethyl-2-(2-methyl benzamido methyl)-3-azabicyclo (3,3,0) octane, M.P. 94° C (cyclohexane), starting from 2-methyl benzoyl chloride and N-ethyl-2-aminomethyl-3-azabicyclo (3,3,0) octane.

12. N-ethyl-2-(2-nitrobenzamido methyl)-3-azabicyclo (3,3,0) octane, M.P. 133° C (isopropanol), starting from 2-nitro benzoyl chloride and N-ethyl-2-aminomethyl-3-azabicyclo (3,3,0) octane.

13. N-ethyl-2-(2-amino benzamido methyl)-3-azabicyclo (3,3,0) octane, M.P. 115° C (cyclohexane), starting from 2-amino benzoyl chloride and N-ethyl-2-aminomethyl-3-azabicyclo (3,3,0) octane.

14. N-ethyl-2-(4-sulfamoyl benzamido methyl)-3-azabicylo (3,3,0) octane, M.P. 235°–236° C (isopropanol), starting from 4-sulfamoyl benzoyl chloride and N-ethyl-2-aminomethyl-3-azabicyclo (3,3,0) octane.

15. N-ethyl-2-(3-sulfamoyl benzamido methyl)-3-azabicyclo (3,3,0) octane, M.P. 110° C (ethyl acetate), starting from 3-sulfamoyl benzoyl chloride and N-ethyl-2-aminomethyl-3-azabicyclo (3,3,0) octane.

16. N-ethyl-2-(4-fluoro benzamido methyl)-3-azabicyclo (3,3,0) octane, M.P. 112°–113° C (isopropanol/water), starting from 4-fluorobenzoyl chloride and N-ethyl-2-aminomethyl-3-azabicyclo (3,3,0) octane.

17. N-ethyl-2-(2-hydroxy benzamido methyl)-3-azabicyclo (3,3,0)octane, B.P. /0,1mmHg 175°–178° C, starting from 2-hydroxybenzoyl chloride and N-ethyl-2-amino methyl-3-azabicyclo (3,3,0) octane.

18. N-ethyl-7-(3-sulfamoyl-4-chloro benzamido methyl)-8-azabicyclo (4,3,0) nonane, M.P. of its hydrochloride : 262°–264° C (acetic acid), starting from 3-sulfamoyl-4-chloro benzoyl chloride and N-ethyl-7-aminomethyl-8-azabicyclo (4,3,0) nonane.

19. N-ethyl-7-(2-methoxy-5-chloro benzamido methyl)-8-azabicyclo (4,3,0) nonane, M.P. of its hydrochloride : 170°–174° C (isopropanol), starting from 2-methoxy-5-chloro benzoyl chloride and N-ethyl-7-aminomethyl-8-azabicyclo (4,3,0) nonane.

EXAMPLE 20

N-ethyl-2-(2-methoxy-4-amino-5-chloro benzamido methyl)-3-azabicyclo (3,3,0) octane

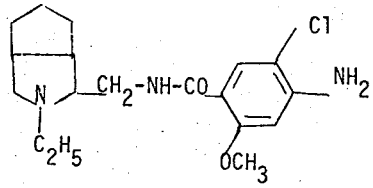

To a suspension of 6 parts of 2-methoxy-4-acetylamino-5-chloro benzoic acid in 50 parts of anhydrous tetrahydrofuran, were added 2.5 parts of triethylamine. The solution thus obtained was poured portionwise in a mixture of 2.7 parts of ethyl chloroformate in 80 parts of tetrahydrofuran maintained at 0° C. After stirring for 10 minutes, 4.1. parts of N-ethyl-2-aminomethyl-3-azabicyclo (3,3,0) octane were added. After being maintained at room temperature for 10 minutes, the temperature was progressively increased and, finally, the reaction mixture was refluxed for 60 minutes. After cooling the mixture was filtered and the filtrate was evaporated in vacuo. After recrystallization in 50 parts of ethyl acetate, there were obtained 5.5. parts of N-ethyl-2-(2-methoxy-4-acetylamino-5-chloro benzamido methyl)-3-azabicyclo (3,3,0) octane, M.P. 156°–157° C (ethyl acetate).

7 parts of N-ethyl-2-(2-methoxy-4-acetylamino-5-chloro benzamido methyl)-3-azabicyclo (3,3,0) octane were heated for 30 minutes in the presence of 17.7 parts of a 2N solution of sodium hydroxide and 15 parts of ethanol. After cooling, the precipitate was filtered and recrystallized in 40 parts of acetonitrile. There were obtained .5 parts of N-ethyl-2-(2-methoxy-4-amino-5-chloro benzamido methyl)-3-azabicyclo(3,3,0) octane, M.P. 128°–129° C.

EXAMPLES 21 – 22

The following compounds were prepared according to the process described in Example 20.

21. N-ethyl-7-(2-methoxy-4-amino-5-chloro benzamido methyl)-8-azabicyclo (4,3,0)nonane, M.P. 165° C (isopropanol) starting from 2-methoxy-4-acetylamino-5-chloro benzoic acid and N-ethyl-7-aminomethyl-8-azabicyclo (4,3,0)nonane.

22. N-allyl-2-(2-methoxy-4-amino-5-chloro benzamido methyl)-3-azabicyclo (3,3,0) octane, M.P. 115° C (acetonitrile) starting from 2-methoxy-4-acetyl amino-5- chloro benzoic acid and N-allyl-2-aminomethyl-3-azabicyclo (3,3,0) octane.

We claim:
1. A compound selected from the group consisting of:
   A. Disubstituted azabicycloalkanes of the general formula I:

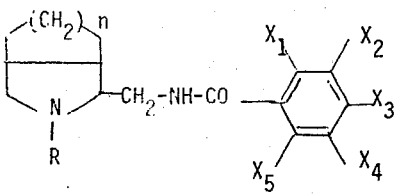

I wherein:
   n is 2;
   R is selected from the group consisting of saturated and unsaturated aliphatic hydrocarbon having from 1 to 5 carbon atoms inclusive in straight and branched chain, and,
   $X_1$, $X_2$, $X_3$, $X_4$ and $X_5$ are each selected from the group consisting of hydrogen, halogen, hydroxy, alkyl and alkoxy each having from 1 to 5 carbon atoms inclusive, trifluoromethyl, nitro, amino, and sulfamoyl, and,
   B. Physiologically tolerable acid addition salts thereof.

2. A compound of claim 1 which is N-ethyl-7-(2-methoxy-5-sulfamoyl benzamido methyl)-8-azabicyclo (4,3,0) nonane.

3. A compound of claim 1, which is N-ethyl-7-(3-sulfamoyl-4-chloro benzamido methyl)-8-azabicyclo (4,3,0)nonane hydrochloride.

4. A compound of claim 1, which is N-ethyl-7-(2-methoxy-5-chloro benzamido methyl)-8-azabicyclo (4,3,0) nonane hydrochloride.

5. A compound of claim 1, which is N-ethyl-7-(2-methoxy-4-amino-5-chloro benzamido methyl)-8-azabicyclo (4,3,0) nonane.

6. A pharmaceutical composition containing as active principle a compound of claim 1 in an amount of 10 to 200 mg preferably of 20 to 100 mg, together with a suitable pharmaceutical carrier.

7. The composition of claim 6, wherein the active principle is the compound of claim 2.

8. The composition of claim 6, wherein the active principle is the compound of claim 3.

9. The composition of claim 6, wherein the active principle is the compound of claim 4.

10. The composition of claim 6, wherein the active principle is the compound of claim 5.

11. A method for treating a living animal body afflicted with gastroduodenal ulcer, gastric hypertension, nauseous syndromes of central origin or hypertension, comprising the step of administering an amount of a compound of claim 1 which is effective for the alleviation of the said condition.

12. The method of claim 11, wherein the compound administered is the compound of claim 2.

13. The method of claim 11, wherein the compound administered is the compound of claim 3.

14. The method of claim 11, wherein the compound administered is the compound of claim 4.

15. The method of claim 11, wherein the compound administered is the compound of claim 5.

* * * * *